United States Patent [19]

Hulls et al.

[11] 4,081,367

[45] Mar. 28, 1978

[54] PURIFICATION OF WASTE WATER HIGH IN CARBOHYDRATES AND SIMULTANEOUS PRODUCTION OF HIGH PROTEIN FEED PRODUCT

[75] Inventors: John Robin Hulls, Mill Valley; David Michael Donofrio, Stinson Beach, both of Calif.

[73] Assignee: Bio-Kinetics Inc., San Rafael, Calif.

[21] Appl. No.: 761,765

[22] Filed: Jan. 24, 1977

[51] Int. Cl.² .............................................. C02C 5/10
[52] U.S. Cl. ........................................ 210/11; 210/14; 210/15; 195/82; 426/53
[58] Field of Search ................... 210/2, 11, 15, 18, 14; 426/48, 52–54, 60; 195/82

[56] References Cited

U.S. PATENT DOCUMENTS

| | | | |
|---|---|---|---|
| 3,105,799 | 10/1963 | Tveit | 195/82 |
| 3,361,555 | 1/1968 | Herschler | 210/11 |
| 3,580,840 | 5/1971 | Uridil | 210/11 |
| 3,751,338 | 8/1973 | Farris | 210/11 |
| 3,860,488 | 1/1975 | Cooper | 195/82 |

Primary Examiner—Charles N. Hart
Assistant Examiner—Benoit Castel
Attorney, Agent, or Firm—Owen, Wickersham & Erickson

[57] ABSTRACT

A method for purifying waste water high in carbohydrate while obtaining therefrom a high-protein feed product. The waste water is inoculated with yeast of the type that converts starch and sugars into more yeast. The pH is adjusted to desired levels, and then the inoculated waste is circulated and recirculated in conjunction with air in amounts that enhance the growth rate of the yeast. The purified liquid waste is then separated from moist solids, and a large proportion of the moist solids is harvested as feed material, while a smaller proportion is taken for use in recycle. The proportion to be recycled is sent to a treatment zone where the pH is lowered to approximately 3.5 and where antibiotics are added, the lowering of the pH and the antibiotics both serving to suppress a substantial portion of bacterial growth while enabling the yeast to grow. After a suitable dwell time, the treated material is used in the inoculating step as the inoculant.

4 Claims, 4 Drawing Figures

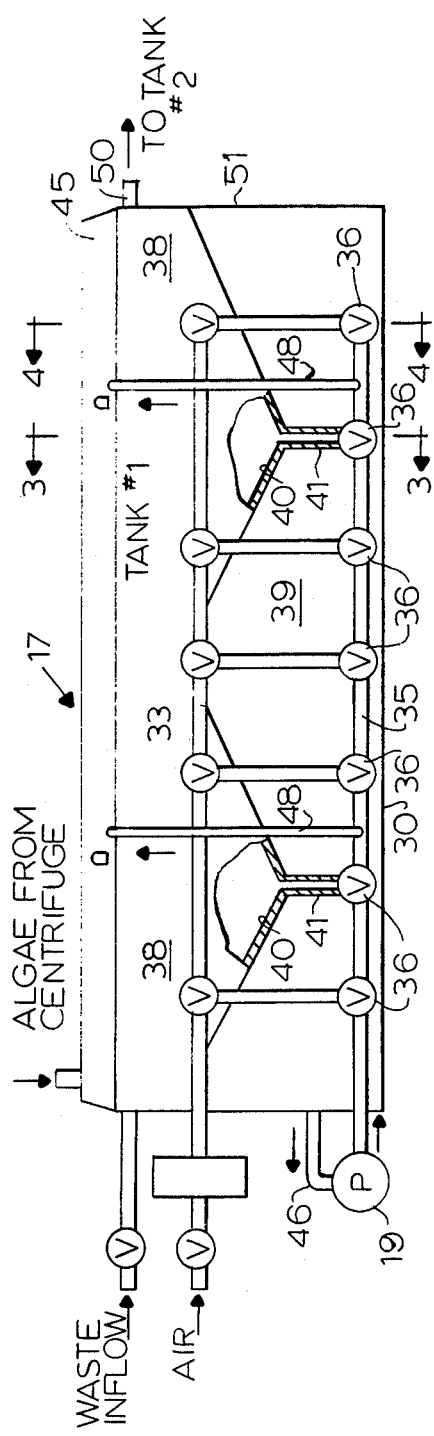
FIG.2
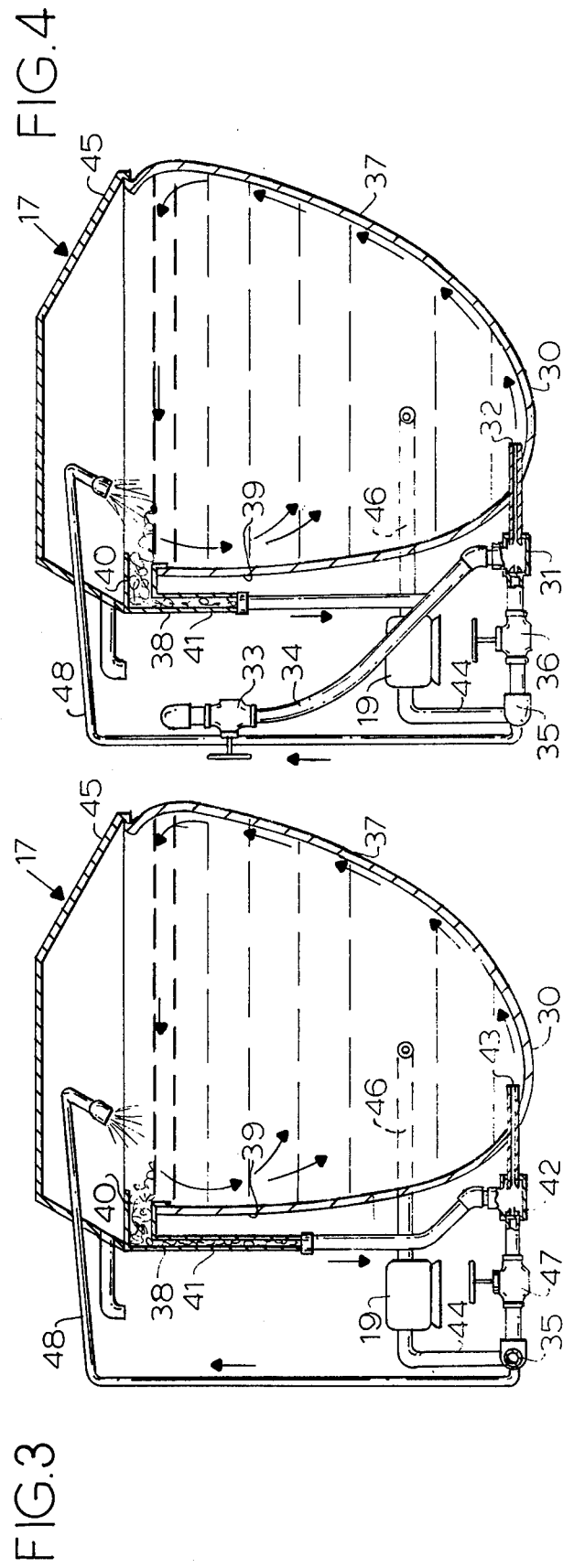
FIG.3
FIG.4

PURIFICATION OF WASTE WATER HIGH IN CARBOHYDRATES AND SIMULTANEOUS PRODUCTION OF HIGH PROTEIN FEED PRODUCT

BACKGROUND OF THE INVENTION

This invention relates to the purification of waste water which is high in carbohydrates including starch and at the same time enables obtaining from this high carbohydrate water a harvest of single-celled protein which can be used to feed chickens and other animals. Thus, the cost of the necessary purification is at least partially recovered in the ability to sell the harvest.

The invention is particularly useful in the processing of waste from potatoes and other high starch products as well as from products high in sugar.

For example, in the potato processing industry heretofore the waste treatment plants have been simple adaptations of municipal waste treatment techniques. The direct applications of aerated lagoons and other conventional treatment systems has resulted in major difficulties from anaerobic conditions and also the problem of the solids bulking in final clarifiers. There has been a great deal of public pressure on the regulatory agencies to overcome the pollution which is met when the waste is simply dumped into the rivers and streams or left in these lagoons to develop a smelly and objectionable product while undergoing such purification as is there undergone.

In the present invention a fully aerobic system operates in quite a short time to convert the non-sterile starch, sugar, and other wastes into single-celled protein organisms which can thereupon be separated from the effluent, as by centrifuging, so that the effluent itself has been sufficiently purified for unobjectionable feeding into streams and the like, while the single-celled protein material can be largely harvested, dried, and used to feed chickens and other such animals.

SUMMARY OF THE INVENTION

In the present invention the high-ccarbohydrate water whether it contains sugar or starch or both of these, as well as other nutrients, is inoculated with yeast of the type that converts starch to glucose and consumes other nutrients, while producing more yeast, the yeast being single-celled protein organisms. For example, the yeast may be *Candida utilis, Candida tropicalis,* or a mixture of *Candida utilis* and *Candida tropicalis,* which may be in equal proportions. Other suitable yeasts may, however, be used. If the waste is largely sugar, a non-amylitic yeast may be used. Sufficient yeast is used to consume a major portion of the sugar, and other nutrients available to the yeast and convert them to more yeast of the same species, and to by-products such as carbon dioxide. For example, yeast in an amount between 1% and 2% by weight of the dry solids in the culture media consumes about 80% of the waste, the remaining 20% being materials not consumable by the yeast and normally disposable by conventional means. After the original addition of yeast the yeast necessary to continue the operation is derived from the recirculated ferment mass, as shown below. With the pH adjusted initially to 5.0, the inoculated waste water is circulated and recirculated a number of times in conjunction with streams of air (which may, for example, be bubbled through the waste water) in an amount to provide adequate oxygen for the yeast to digest the waste and convert it to more yeast and carbon dioxide. Enough air is used to maintain oxygen dissolved in the culture at all times. The process may be operated on a substantially continuous or actually continuous basis. Within a relatively short time the material is in a status where the yeast has completely consumed the starch material and converted it to more yeast. At this time the material is sent to a centrifuge or other separator device to separate a solids-free liquid from a moist solid material. The solids-free liquid is sufficiently purified to enable its use as desired in the plant or to enable it to be fed to a stream without defiling the stream.

The solids material that has been separated out from this mixture is then divided into two streams, one of which, the principle amount, e.g., about 75%, is harvested and sent to a drier and then used as a chicken feed, cattle feed, hog feed, or other animal feed, for this is most yeast, which is a single-cell protein organism. The smaller proportion, e.g., about 25%, of the solids material, still moist, is sent to a treatment zone, where it may again be rediluted with water, if desired, and then treated in that zone with at least one antibiotic while also lowering the pH to about 3.5 so that the yeast is able to grow, while bacterial growth is suppressed. Then after a suitable dwell time, this material is recycled back to the incoming waste and used as the inoculant there.

Other objects, advantages and features of the invention will appear from the following description of some preferred forms of the invention.

BRIEF DESCRIPTION OF THE DRAWINGS

In the drawings:

FIG. 2 is a view in elevation and partially in section of one of the processing tanks.

FIG. 3 is a view taken along the line 3—3 in FIG. 2 and shows one of the tanks in section.

FIG. 4 is a similar view in section taken along the line 4—4 of FIG. 2.

DETAILED DESCRIPTION OF SOME PREFERRED EMBODIMENTS

Figure 1:
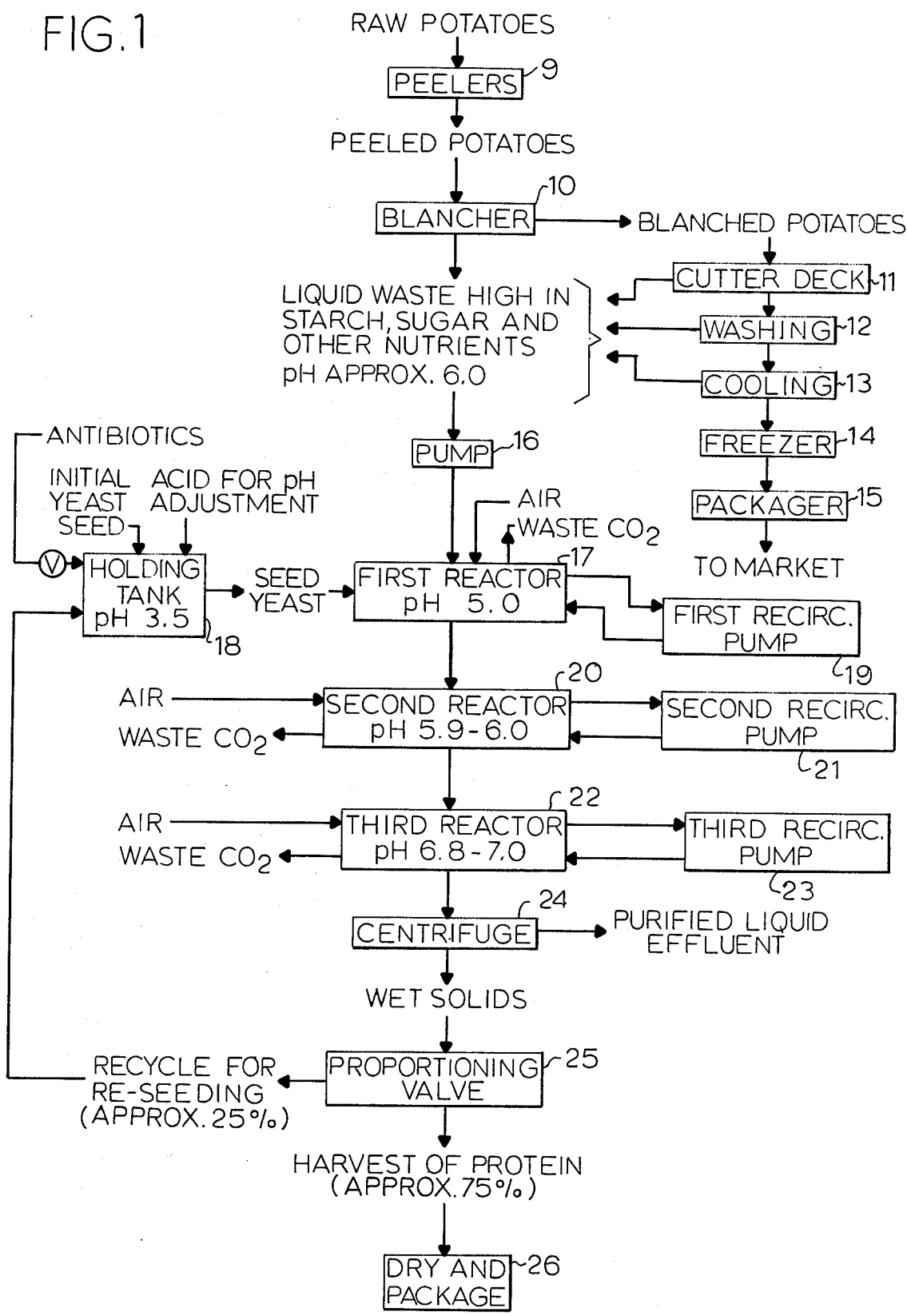
FIG. 1 is a flow sheet of a process embodying the principles of the invention and used in this case with the wastes from the blanching step of processing potatoes.

FIG. 1 is a flow sheet that shows a process in which the invention is applied to purifying the effluent from the blancher in a potato plant. Thus, peeled potatoes from a peeler 9 are fed to a blancher 10 from which blanched potatoes are withdrawn. The blanched potatoes are typically sent to a cutter deck 11, and from there to a washer 12. The cut, blanched, washed potatoes are then sent to a cooler 13 and from there to a freezer 14, whence they go to a package 15 and from there to market.

Waste comes from the blancher 10, the cutter deck 11, the washer 12, and the cooler 13. This liquid waste is high in potato starch and contains some potato sugar, as well as other nutrient material, high in nitrogen, potassium, phosphorous, and has some trace minerals. This waste is withdrawn through a pump 16 and sent to a first reactor 17. Here the liquid waste is injected with an inoculant from a holding tank 18.

When the plant is first started up, the holding tank 18 contains a seed yeast adjusted to a desired pH, so that when the seed yeast is mixed with the liquid potato waste a pH of 5 is achieved in the first tank 17, thereby enabling maximum growth of the yeast. As will be seen later on, once the plant has been started, it is able to maintain itself by a recycling operation, so that it will still be a high-yeast inoculant substantially like that of the original. The yeast is chosen to give a high conversion of the carbohydrate material into additional yeast. Such a yeast is *Candida utilis*, and another one is *Candida tropicalis*, and in an advantageous mode of procedure these are used together, preferably in equal amounts. *Candida utilis* directly takes up or consumes a wide range of sugars in the waste, while *Candida tropicalis* is an amylitic yeast which has the enzyme amylase that acts to break the potato starch down to a sugar such as glucose; *Candida tropicalis* also consumes some of this glucose, but not all. Thus, with the two yeasts in the same treatment tank, the *Candida tropicalis* breaks down the potato starch into glucose for its own use and also produces a surplus, while the *Candida utilis* is consuming the glucose to produce more of its species. The two species work well and continue to produce these species in equal amounts. They also make use of available materials containing yeast—digestible nitrogen, phosphorus, and potassium, as well as trace minerals, all of which help the yeasts to grow better. A by-product is carbon dioxide, which passes off into the air.

With the first reactor 17 preferably maintained at a pH of 5.0 (and at least in the range of 3.5 to 7.0), the operation proceeds relatively rapidly, if the material is kept in an aerobic state. To ensure that this is so, a recirculation pump 19 is provided, and also air and carbon dioxides are provided to the first reactor 17 during the recirculation, so that the first reactor 17 is supplied with air in an amount sufficient to enhance the growth of the yeast organisms. A suitable structure for carrying out this process will be described later.

While all this operation may be done in a single reactor 17 it is preferred to send the material from the first reactor 17 to a second reactor 20 having its own recirculation pump 21 and also being supplied with air substantially the same amount as that for the first reactor 17. The second reactor 20, due to the process going on will have an initial pH of about 5.9 to 6.0. Similarly, good results are obtained by sending the effluent from the second reactor 20 to a third reactor 22 having its own recirculation pump 23 and also being supplied with air. The initial pH in the third tank 22 is about 6.8 to 7.0.

In these series of reactors 17, 20, and 23 (or, if desired, one large reactor, although the series is better), the yeasts are able to digest the waste and convert it into additional yeast.

By regulating the feed of liquid and the size of the tanks 17, 20, and 23, it is possible to keep this process on a continuous basis and to feed the output from the third reactor 22 to a centrifuge 24 where most of the liquid is separated as a purified liquid effluent, suitable either for reuse in the plant or for dumping in a stream without defiling the stream and while maintaining the required environmental purity. The remainder of the liquid in the mixture with solids is then fed to a proportioning valve 25 from which a desired protein harvest (typically about 75% of the yeast) is withdrawn and sent to a drying and packaging station 26. This material is suitable for use as the animal feed.

The proportioning valve 26 also sends out a much smaller proportion (typically about 25%) of the wet solids for use as a recycle for reseeding, and this is a very important part of the invention. This material is sent back to the holding tank 18 in conjunction with a suitable liquid. If this material were simply reused it would be too high in bacteria and the process would be defeated. It is important to enable the yeast to grow at this stage while suppressing the growth of the bacteria. This may be done by holding it in a separate or holding zone, such as the holding tank 18, and using additional acid to lower its pH to a level of about 3.5—no lower— where the bacteria that tend to contaminate the system are unable to grow; the preferred yeast can grow as long as the pH does not drop below 3.5. In any event, the pH is kept at some level where the yeast still grows and the bacteria do not grow. Thus, for this purpose, the pH may be held at about 3.5. At this pH the yeasts mentioned above are able to grow quite satisfactorily, but the bacteria are not. The operation may be further enhanced by the use of a suitable antibiotic, such as the product sold under the proprietary name "Fluorozolodine" which is a synthesized, tetracycline made by Krakow Pharmaceutical Company of Krakow, Poland.

It may be noted that although the pH is adjusted to 3.5 within the tank 18, the somewhat more alkaline potato waste (pH about 6) plus the action of the yeast itself, will in the first reactor 17 readjust the pH up to the desired level of approximately 5.0, will adjust the pH in the second tank 20 up to about 6.0 and will adjust the pH in the third reactor 22 to about 6.8 to 7.0, for optimum growth of the single-celled protein organisms there.

Peeling waste is very caustic, containing sodium hydroxide or sodium carbonate. If peeling waste is introduced into the system, acid, such as sulfuric acid, is used to adjust the pH in the tank 18 to about 5.0.

It may be noted that the initial inoculant may be more easily started in the holding tank 18 before it is used in the first reactor 17.

As an example of the quantities in operation, the pump 16 may supply about 70 gallons a minute, or approximately 100,000 gallons per day to the first reactor 17. Each of the three reactors 17, 20, and 22 may have a capacity of about 6,666 gallons for a total of 20,000 gallons among the three. The inoculant which is a culture of the yeast on a suitable broth such as Difco YM broth, may be put in a tank 18 having a capacity of about two hundred gallons, and, before operation begins, the yeast is enabled to grow for from 4 to 6 hours. Then in the tank 17 approximately two thousand gallons of the waste are mixed with about ten gallons of the inoculant, and the system is run at about thirty gallons per minute of additional waste until the system is filled. From then on it may be operated at its full capacity, here about seventy gallons per minute. The yeast is recirculated in an amount able to maintain the value in the holding tank 18 allowing for the suitable waiting period of again about 4 to 6 hours at a pH of about 3.5 with the addition of the antibiotics as needed.

The reactor 17 may be made from mild steel lined with a Food-and-Drug-Administration approved coating, such as an approved epoxy or phenolic resin, or it may be made from molded plastic, from stainless steel, or from concrete coated or covered with a suitable plastic, such as polypropylene. At the base 30 of the reactor 17 (See FIG. 4) is a series of the injectors 31, having an outlet 32, each being connected to a manifold 33 by a pipe 34. Each injector 31 is also connected to the recirculation pump 19 (FIGS. 1 and 2) by a second manifold 35 and a control valve 36 at each injector 31. Advantageously, the injectors 31 are horizontally disposed across a portion of the base 30 of the reactor 17. The combination of the parabolic configuration of the back wall 37 with the injectors 31 has been found to provide suitable agitation and circulation. Thus, the fluid-gas stream from the injectors 31 cause a portion of the culture to flow up the wall of the reactor 17, following the parabolic arc and establishing a lenticular flow, thereby causing the flowing stream to traverse the upper portion of the reactor 17. This gives very good agitation and a thorough mixture.

An anti-foaming agent may be used to suppress foam in the waste, but in case it is insufficient or would have to be used in quantities that would be uneconomical or would degrade the oxygen transfer, a plurality of foam-offtake conduits 38 is disposed at the front wall 39 of the reactor 17 to skim off foam which may form thereon. The tank 17 is covered with a suitable lid 45, through which extends a foam overflow line. The conduits 38 have a broad V-shaped upper portion 40 leading into pipes 41 at the lower end, which connect there to associated injectors 42 (FIG. 3) having injector outlets 43. The injectors 42 create a vacuum force in the conduits 38, causing the foam to break up; they are also connected to the recirculation pump 19 by conduits 44 and are individually controlled by valves 47. The injectors 42 recycle the foam to the reactor 17. The intake side of the pump 19 is connected to the reactor 17 by a pipe 46, so that the pump 19 recycles a portion of the circulating mass from the reactor 17 through the various injectors 31 and 42 back into the reactor 17. With some waste, it is advantageous to include a series of foam breakup nozzles 47 connected by a pipe 48 to the manifold 35; the nozzle is directed against the foam from above and is directed toward the foam-offtake pipe 38.

In this embodiment, the reactor 17 is provided with an outlet pipe 50 (FIG. 2) at the upper or top portion of the end wall 51 to conduct treated material to a second reactor 20 having the same structure as the reactor 17. The reactor may typically be 10 feet wide, 10 feet high, and 30 feet long.

To those skilled in the art to which this invention relates, many changes in construction and widely differing embodiments and applications of the invention will suggest themselves without departing from the spirit and scope of the invention. The disclosures and the description herein are purely illustrative and are not intended to be in any sense limiting.

We claim:

1. A method for purifying waste water that is high in carbohydrates including starch while obtaining therefrom a high-protein feed product, comprising the steps of:

inoculating said waste water at a pH of approximately 6, with yeast inoculant that converts starch, sugar and nutrients to more yeast, and in an amount sufficient to so convert substantially all the starch, sugar and yeast consumable nutrients in said waste water, said inoculant being at a pH such that a mixture of waste water and inoculant is adjusted to approximately 5, growing said inoculated yeast in said waste water while
the pH in said water-inoculant mixture increases gradually from an initial value of approximately 5, toward neutrality as a by-product of the growth of the yeast without addition of further materials,
circulating and recirculating the inoculated water with air in an amount that enhances the growth rate, and
venting waste $CO_2$ to atmosphere,
separating out purified liquid waste from moist solids, at the time when the pH is about 7,
harvesting a large proportion of moist solids, while selecting a smaller proportion for recycle,
sending said smaller proportion to a treatment zone,
treating it there with at least one antibiotic and lowering the pH there to about 3.5, by addition of acid, both to suppress a substantial portion of bacterial growth while the yeast grows, and then, after a suitable treatment time,
recycling the treated material to said inoculating step as the inoculant yeast.

2. The method of claim 1 wherein said growing step is done in three zones while adjusting the pH in the three zones to respective successive value of about 5.0, up to about 6.0, and up to about 7.0.

3. A method for purifying waste water that is high in carbohydrates while obtaining therefrom a high-protein feed product, comprising the steps of:

inoculating said waste water at a pH of approximately 6 with a yeast inoculant that converts said carbohydrate to reproduce additional yeast organisms,
growing said inoculated yeast while
adjusting the pH in said inoculated water to an initial value of approximately 5, by addition of the yeast inoculant at a pH of about 3.5, the pH of the mixture thereafter gradually rising as the yeast grows,
circulating and recirculating the inoculated water in conjunction with air in an amount that enhances the growth rate, and
venting waste $CO_2$ to atmosphere,
separating out purified liquid waste from moist solids, when the pH of the mixture is approximately 7,
harvesting a large proportion of moist solids, while selecting a smaller proportion of recycle,
sending said smaller proportion to a treatment zone,
treating it there with antibiotics and lowering the pH there by addition of acid to about 3.5, both to suppress a substantial portion of bacterial growth while the yeast grows, and then, after a suitable treatment time,
recycling the treated material to said inoculating step as the inoculant yeast.

4. The method of claim 3 wherein said growing step comprises three stages, and
adjusting the pH in the respective stages successively to about 5.0, up to about 6.0, and up to about 7.0.

* * * * *

UNITED STATES PATENT AND TRADEMARK OFFICE
CERTIFICATE OF CORRECTION

PATENT NO. : 4,081,367
DATED : March 28, 1978
INVENTOR(S) : JOHN ROBIN HULLS & DAVID MICHAEL DONOFRIO It is certified that error appears in the above-identified patent and that said Letters Patent are hereby corrected as shown below:

In the drawings, at the top of Fig. 2, "ALGAE FROM CENTRIFUGE" should read --SEED YEAST--; near the top of Fig. 2, delete "TANK #1"; at the right of Fig. 2, "TO TANK #2" should read --TO REACTOR 20--; in the center near the top of Fig. 2, the numeral "33" should have lead lines down to the "Ⓥ" directly below and to the left of "33" and to the "Ⓥ" directly below and to the right of "33".

Column 4, line 31, "tank 18" should read --tank 17--.

Column 1, line 42, "ccarbohydrate" should read
--carbohydrate--.

Column 2, line 18, "most yeast" should read --mostly yeast--.

Column 5, line 58, "such that a" should read --such that the--.

Signed and Sealed this

Twenty-fourth Day of October 1978

[SEAL]

Attest:

RUTH C. MASON
Attesting Officer

DONALD W. BANNER
Commissioner of Patents and Trademarks